(12) United States Patent
Hill et al.

(10) Patent No.: US 6,936,732 B2
(45) Date of Patent: Aug. 30, 2005

(54) SULPHONATION OF PHENOLS

(76) Inventors: Jonathan Simon Hill, 45 Overdale Crescent, Flixton, Manchester (GB), M41 5GR; Bernard Capai, 28 Rue de la Gare, Viarmes (FR), 95270; Carlo Neri, Via Europa 32, 20097 San Donato Milanese, Milan (IT)

( * ) Notice: Subject to any disclaimer, the term of this patent is extended or adjusted under 35 U.S.C. 154(b) by 0 days.

(21) Appl. No.: 10/490,361
(22) PCT Filed: Sep. 18, 2002
(86) PCT No.: PCT/GB02/04218
§ 371 (c)(1),
(2), (4) Date: Oct. 1, 2004
(87) PCT Pub. No.: WO03/027063
PCT Pub. Date: Apr. 3, 2003

(65) Prior Publication Data
US 2005/0054876 A1 Mar. 10, 2005

(30) Foreign Application Priority Data
Sep. 22, 2001 (GB) .............................. 0122903

(51) Int. Cl.[7] ............................................. C07C 309/00
(52) U.S. Cl. ............................................ 562/45; 562/46
(58) Field of Search ..................................... 562/45, 46

(56) References Cited
U.S. PATENT DOCUMENTS
3,468,938 A   9/1969  Confranceso et al.

FOREIGN PATENT DOCUMENTS
FR   2791057        9/2000
GB   250241         4/1927
JP   09227499 A2    9/1997
JP   09-227499   *  9/1997

* cited by examiner

*Primary Examiner*—Paul A. Zucker
(74) *Attorney, Agent, or Firm*—Baker & Daniels LLP

(57) ABSTRACT

A process for the preparation of sulphonated phenols of general formula (I) where $R_1$ is hydrogen, a $C_1-C_{20}$ alkyl group which is unsubstituted or substituted by halogen, cyano, hydroxyl, $C_1-C_{20}$ alkoxy, $C_2-C_{20}$ alkoxycarbonyl, acyloxy and/or phenyl which is unsubstituted or substituted by $C_1-C_4$ alkyl, $C_1-C_4$ alkoxy and/or halogen, $R_2$ is hydrogen, $C_1-C_{20}$ alkyl or benzoyl of general formula (II) where $R_3$ and $R_4$ independently of one another are each hydrogen, halogen, $C_1-C_{12}$ alkyl, $C_1-C_{12}$ alkoxy, $C_1-C_4$ haloalkyl, $C_3-C_8$ cycloalkyl, $C_4-C_{12}$ cycloalkylalkyl, cyano, hydroxyl, or hydroxyethyl or are each phenoxy, $C_7-C_{10}$ phenylalkyl or phenyl which is unsubstituted or substituted by $C_1-C_4$ alkyl, $C_1-C_4$ alkoxy and/or halogen, and $R_5$ is hydrogen or the group $SO_3X$ where X can be hydrogen, a monovalent metal or a group —$N(R_6)_3$, where each of the three radicals $R_6$ can be independently of one another hydrogen, $C_1-C_6$ alkyl or $C_1-C_6$ hydroxy alkyl, which process comprises reacting a phenol of general formula (III) where $R_1$ and $R_2$ are as defined above, with a halosulphonic acid in a solvent which is a mixture of a $C_5-C_{10}$ aliphatic or cycloaliphatic hydrocarbon and a dialkyl carbonate of general formula (IV) $R_7$—O—CO—O—$R_8$ where $R_7$ and $R_8$ each represent independently a $C_1-C_4$ alkyl group

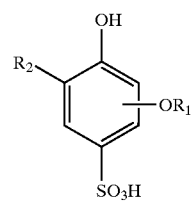

(I)

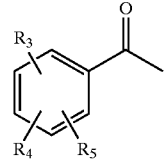

(II)

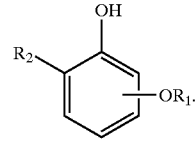

(III)

20 Claims, No Drawings

SULPHONATION OF PHENOLS

This invention relates to a novel and improved process for the preparation of sulphonated phenols.

Sulphonated phenols are widely used as dyes, medical intermediates, photo-developing chemicals and cosmetic preparations. In particular, 4-alkoxy-2-hydroxybenzophenone-5-sulphonic acids are suitable as UV absorbers in sun screening preparations.

It is known that phenols can be readily sulphonated with sulphuric acid, sulphur trioxide gas, dialkyl sulphuric acid and chlorosulphonic acid etc. The reaction is usually carried out in a solvent.

Solvents which have been used in the sulphonation of phenols include nitrobenzene, nitromethane, alkyl ethers, cyclic ethers, aliphatic hydrocarbons, chlorohydrocarbons and dialkyl carbonates, all of which present undesirable problems. For example, nitro solvents and alkyl ethers have a high risk of explosion and some cyclic ethers are extremely harmful and are not suited for the above mentioned uses of sulphonated phenols.

U.S. Pat. No. 3,468,938 and U.S. Pat. No. 3,696,077 disclose that 4-alkoxy-2 hydroxybenzophenones are reacted with chlorosulphonic acid in a chlorohydrocarbon solvent, e.g. 1,2 dichlorethane. However, this process has a number of disadvantages. For example, the toxicity of the stated solvents causes problems.

Japanese Patent Application Publication Number H9-227499 describes a method of sulphonating phenols using chlorosulphonic as sulphonating agent and dialkyl carbonates as solvent, e.g. dimethyl carbonate, diethyl carbonate and di-isopropyl carbonate. French Patent Application Number 2791057 also describes the use of dialkyl carbonates as a solvent in the preparation of 4-alkoxy-2-hydroxybenophenone-5-sulphonic acids. Aryl sulphonic acids are, however, thermally unstable when dissolved in hot dialkyl carbonates leading to degradation, loss of yield and contamination of the product. Moreover, French Patent Application Number 2791057 also states that the use of aliphatic hydrocarbons of 5–8 carbon atoms cause problems of colouration and the formation of by-products which affect the purity of the final product.

U.S. Pat. No. 5,072,034 describes a method of preparing-4-alkoxy-2--hydroxybenzophenone-5-sulphonic acids by reacting a 4-alkoxy-2-hydroxybenzophenone with chlorosulphonic acid wherein the reaction is carried out in carboxylic ester solvents, e.g. ethyl acetate. These are not satisfactory solvents because degradation leads to the formation of carboxylic acids which impart undesirable odour to the product.

It is an object of the present invention to provide a novel and improved process for the preparation of sulphonated phenols which overcomes the disadvantages of the known processes.

According to the present invention there is provided a process for the preparation of sulphonated phenols of the general formula I

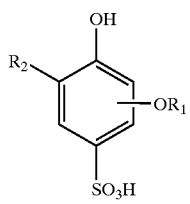

I where $R_1$ is hydrogen, a $C_1$–$C_{20}$ alkyl group which is unsubstituted or substituted by halogen, cyano, hydroxyl, $C_1$–$C_{20}$ alkoxy, $C_2$–$C_{20}$ alkoxycarbonyl, acyloxy and/or phenyl which is unsubstituted or substituted by $C_1$–$C_4$ alkyl, $C_1$–$C_4$ alkoxy and/or halogen, $R_2$ is hydrogen, $C_1$–$C_{20}$ alkyl or benzoyl of the general formula II

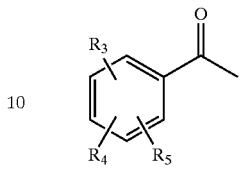

II where $R_3$ and $R_4$ independently of one another are each hydrogen, halogen, $C_1$–$C_{12}$ alkyl, $C_1$–$C_{12}$ alkoxy, $C_1$–$C_4$ haloalkyl, $C_3$–$C_8$ cycloalkyl, $C_4$–$C_{12}$ cycloalkylalkyl, cyano, hydroxyl, or hydroxyethyl or are each phenoxy, $C_7$–$C_{10}$ phenylalkyl or phenyl which is unsubstituted or substituted by $C_1$–$C_4$ alkyl, $C_1$–$C_4$ alkoxy and/or halogen, and $R_5$ is hydrogen or the group $SO_3X$ where X can be hydrogen, a monovalent metal or a group $-N(R_6)_3$, where each of the radicals $R_6$ can be independently of one another hydrogen $C_1$–$C_6$ alkyl or $C_1$–$C_6$ hydroxy alkyl, which process comprises reacting a phenol of the general formula III

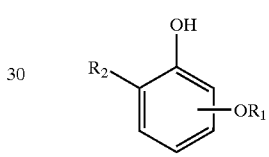

III where $R_1$ and $R_2$ are as defined above, with a halosulphonic acid in a solvent which is a mixture of a $C_5$–$C_{10}$ aliphatic or cycloaliphatic hydrocarbon and a dialkyl carbonate of the general formula IV

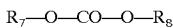

$$R_7\text{—}O\text{—}CO\text{—}O\text{—}R_8 \qquad \text{IV}$$

where $R_7$ and $R_8$ each represent independently a $C_1$–$C_4$ alkyl group.

The phenol of the general formula III preferably is catechol, resorcinol, hydroquinone or a benzophenone.

The preferred benzophenone is a 4-alkoxy-2-hydroxybenzophenone.

The preferred halosulphonic acid is chlorosulphonic acid.

Preferably, the dialkyl carbonate in the solvent mixture is dimethyl carbonate, diethyl carbonate or di-isopropyl carbonate.

Further preferably, the aliphatic or cycloaliphatic hydrocarbon in the solvent mixture is hexane, cyclohexane, methylcyclohexane, heptane, isooctane, isononane or decane.

The process of the invention conveniently is carried out with an excess of the phenol of general formula III over the halosulphonic acid, preferably an excess of 2 to 5 mol % of the phenol.

The process of the invention furthermore is conveniently carried out with the concentration of phenol of the general formula III in the solvent mixture being 5 to 50% w/w, preferably 15 to 30% w/w.

The dialkyl carbonate solvent and the aliphatic or cycloaliphatic hydrocarbon solvent are mixed in a weight ratio of from 10:90 to 90:10, preferably 40:60 to 60:40.

Preferably, the process of the invention is carried out at a temperature between −10° C. to 80° C.

Conveniently the sulphonation reaction is carried out at a temperature between 0° C. to 30° C. and the products from the sulphonation are then raised gradually to 60° C. to 70° C. to remove acid product from the sulphonation reaction.

Further preferably, the sulphonation reaction is carried out under a pressure between 2 mm and 760 mm.

A particular advantage of using a mixed dialkyl carbonate/aliphatic or cycloaliphatic hydrocarbon solvent according to the invention is that it allows reflux at lower temperatures to facilitate removal of biproduct acid (e.g. HCl) from the sulphonation reactor. A further advantage is that the mixed solvent acts to reduce the solubility of the sulphonated product in the solvent thereby facilitating easy recovery of the product and higher yield of the product. An additional very important benefit of the use of the mixed solvent system is the avoidance of problems of colour and impurities that are observed when an aliphatic hydrocarbon solvent is used on its own.

Aryl sulphonates are generally not very stable (with regard to desulphonation) when dissolved in, for example, dialkyl carbonate solvents. By carrying out the reaction in the mixed solvent, this leads to reduced degradation due to lower temperatures and precipitation of the product In the sulphonation of 4-alkoxy-2-hydroxy benzophenones by the process according to the invention, a sulphonic acid group is, as a rule, introduced into the 4-alkoxy-2-hydroxy nucleus of the starting compound. If the reactivity of the second nucleus has been increased by appropriate substitution with electron donor groups, such as hydroxyl or alkoxy, it is also possible introduce two sulpho radicals. For example, the reaction of 2,2'-dihydroxy-4,4'-dimethoxybenzophenone with two moles of sulphonating agent gives 2,2'-dihydroxy-4,4'-dimethoxybenzophenone-5,5'-disulphonic acid.

With regard to the use of 4-alkoxy-2-hydroxybenzophenone-5-sulphonic acids as UV absorbers, particularly preferred radicals are those in which $R_1$ is $C_1$–$C_{18}$-alkyl, $R_3$ is in the ortho-position to the ketonic carbonyl group and is hydrogen or hydroxyl and $R_5$ is hydrogen. Other important compounds are those in which R1 is $C_1$–$C_{18}$-alkyl, $R_3$ and/or $R_4$ are each hydrogen or $R_3$ is an ortho-hydroxyl group and $R_4$ is a para-alkoxy group, and $R_5$ is hydrogen.

Regarding their use as UV absorbers, particularly suitable compounds are the following:
2-hydroxy-4-methoxybenzophenone-5-sulphonic acid,
2-hydroxy-4-ethoxybenzophenone-5-sulphonic acid,
2-hydroxy-4-n-propoxybenzophenone-5-sulphonic acid,
2-hydroxy-4-isopropoxybenzophenone-5-sulphonic acid,
2-hydroxy-4-n-butoxybenzophenone-5-sulphonic acid,
2-hydroxy-4-isobutoxybenzophenone-5-sulphonic acid,
2-hydroxy-4-sec-butoxybenzophenone-5-sulphonic acid,
2-hydroxy-4-n-pentyloxybenzophenone-5-sulphonic acid,
2-hydroxy-4-n-hexyloxybenzophenone-5-sulphonic acid,
2-hydroxy-4-isohexyloxybenzophenone-5-sulphonic acid,
2-hydroxy-4-n-heptyloxybenzophenone-5-sulphonic acid,
2-hydroxy-4-isoheptyloxybenzophenone-5-sulphonic acid,
2-hydroxy-4-n-octyloxybenzophenone-5-sulphonic acid,
2-hydroxy-4-(3,4-dimethyl-1-hexyloxy)-benzophenone-5-sulphonic acid,
2-hydroxy-4-(3,5-dimethyl-1-hexyloxy)-benzophenone-5-sulphonic acid,
2-hydroxy-4-(4,5-dimethyl-1-hexyloxy)-benzophenone-5-sulphonic acid,
2-hydroxy-4-(3-methyl-1-heptyloxy)-benzophenone-5-sulphonic acid,
2-hydroxy-4-n-nonyloxybenzophenone-5-sulphonic acid,
2-hydroxy-n-decyloxybenzophenone-5-sulphonic acid,
2-hydroxy-4-n-undecyloxybenzophenone-5-sulphonic acid,
2-hydroxy-4-n-dodecyloxybenzophenone-5-sulphonic acid,
2-hydroxy-4-n-hexadecyloxybenzophenone-5-sulphonic acid,
2-hydroxy-4-n-octadecyloxybenzophenone-5-sulphonic acid,
2-hydroxy-4-(2-acetoxyethoxy)-benzophenone-5-sulphonic acid,
2-hydroxy-4-(2-phenbenzoyloxyethoxy)-benzophenone-5-sulphonic acid,
2-hydroxy-4-phenylmethyleneoxybenzophenone-5-sulphonic acid,
2-hydroxy-4-(2-phenylethyleneoxy)-benzophenone-5-sulphonic acid,
2,2'-dihydroxy-4,4'-dimethoxybenzophenone-5-sulphonic acid,
2,2'-hydroxy-4,4'-dimethoxybenzophenone-5,5'-sulphonic acid,
2,2'-dihydroxy-4-methoxybenzophenone-5-sulphonic acid,
2-hydroxy-4'-fluoro-4-methoxybenzophenone-5-sulphonic acid,
2-hydroxy-4-methoxy-4'-methylbenzophenone-5-sulphonic acid,
2-hydroxy-4-methoxy-4'-phenoxybenzophenone-5-sulphonic acid,
2-hydroxy-4-methoxy-4'-chlorobenzophenone-5-sulphonic acid,
2-hydroxy-4-methoxycarbonylmethyleneoxybenzophenone-5-sulphonic acid and
2-hydroxy-4-ethoxycarbonylmethyleneoxybenzophenone-5-sulphonic acid.

EXAMPLES OF THE INVENTION

Example 1

Preparation of 2-Hydroxy-4-methoxybenzophenone-5-sulphonic Acid 145 g (0.634 moles) of 2-hydroxy-4-methoxybenzophenone, 480 g dimethyl carbonate and 320 g cyclohexane were charged under nitrogen to a 4-necked one litre reactor fitted with stirrer, thermometer and condenser attached to an HCl scrubber system. The reaction mixture was heated to 60° C. and 70.4 g (0.604 moles) of chlorosulphonic acid added over a period of 4 h with removal of hydrogen chloride gas. On completion of the addition, the reaction mixture is heated to 70–72° C. for 1 h, and then cooled to 20° C. The product was collected by filtration and washed with dimethyl carbonate/cyclohexane (2×60 g/40 g) and dried under reduced pressure at 50° C. to give 167.5 g (90%) of 2-hydroxy-4-methoxybenzophenone-5-sulphonic acid.

Example 2

Preparation of 2-Hydroxy-4-methoxybenzophenone-5-sulphonic Acid

Example 1 was repeated except diethyl carbonate (480 g) was used instead of dimethyl carbonate yielding 158 g (85%) of 2-hydroxy-4-methoxybenzophenone-5-sulphonic acid.

Example 3

Preparation of 2-Hydroxy-4-methoxybenzophenone-5-sulphonic Acid

Example 1 was repeated except heptane (320 g) was used instead of cyclohexane yielding 152 g (82%) of 2-hydroxy-4-methoxybenzophenone-5-sulphonic acid.

Example 4

Preparation of 2,4-Dihydroxybenzene sulphonic Acid 15.0 g (0.136 moles) of resorcinol, 102 g dimethyl carbonate and 68 g cyclohexane were charged under nitrogen to a 4-necked one litre reactor fitted with stirrer, thermometer and condenser attached to an HCl scrubber system. The reaction mixture was heated to 60° C. and 15.1 g (0.13 moles) of chlorosulphonic acid added over a period of 4 h with removal of hydrogen chloride gas. On completion of the addition, the reaction mixture is heated to 70–72° C. for 1 h, and then cooled to 20° C. The reaction mixture separated into two layers with the lower layer containing 2,4-dihydroxybenzene sulphonic Acid (63.2% by hplc) and resorcinol (31.5% by hplc).

Example 5

Preparation of 1,4-Di-hydroxybenzene sulphonic Acid 15.0 g (0.136 moles) of hydroquinone, 102 g dimethyl carbonate and 68 g cyclohexane were charged under nitrogen to a 4-necked one litre reactor fitted with stirrer, thermometer and condenser attached to an HCl scrubber system. The reaction mixture was heated to 60° C. and 15.1 g (0.13 moles) of chlorosulphonic acid added over a period of 4 h with removal of hydrogen chloride gas. On completion of the addition, the reaction mixture is heated to 70–72° C. for 1 h, and then cooled to 20° C. The reaction mixture separated into two layers with the lower layer containing 1,4-dihydroxybenzene sulphonic acid (60% by hplc) and hydroquinone (38% by hplc).

Example 6

Preparation of 2,4-Di-hydroxy-benzophenone-5-sulphonic Acid 29.0 g (0.136 moles) of 2,4-dihydroxybenzophenone, 102 g dimethyl carbonate and 68 g cyclohexane were charged under nitrogen to a 4-necked one litre reactor fitted with stirrer, thermometer and condenser attached to an HCl scrubber system. The reaction mixture was heated to 60° C. and 15.1 g (0.13 moles) of chlorosulphonic acid added over a period of 4 h with removal of hydrogen chloride gas. On completion of the addition, the reaction mixture is heated to 70–72° C. for 1 h, and then cooled to 20° C. The reaction mixture separated into two layers with the lower layer containing 2,4-dihydroxy-benzophenone-5-sulphonic acid (94.8% by hplc) and 2,4-dihydroxybenzophenone (3.4% by hplc).

Example 7

Preparation of 2-Hydroxy-4-methoxybenzophenone-5-sulphonic Acid 42.4 g (0.13 moles) of 2-hydroxy-4-octyloxybenzophenone, 102 g dimethyl carbonate and 68 g cyclohexane were charged under nitrogen to a 4-necked one litre reactor fitted with stirrer, thermometer and condenser attached to an HCl scrubber system. The reaction mixture was heated to 60° C. and 15.1 g (0.13 moles) of chlorosulphonic acid added over a period of 2 h with removal of hydrogen chloride gas. On completion of the addition, the reaction mixture is heated to 70–72° C. for 1 h, and then cooled to 20° C. The product was collected by filtration and washed with dimethyl carbonate/cyclohexane (52/34 g) and dried under reduced pressure at 50° C. to give 5.8 g of 2-hydroxy-4-octyloxybenzophenone-5-sulphonic acid, and a mother liquor (256 g) containing 2-hydroxy-4-octyloxybenzophenone-5-sulphonic acid (82.4% by hplc) and 2-hydroxy-4-octyloxybenzophenone (16% by hplc).

Examples 8–13

The following table describes the effect of different ratios of dimethyl carbonate (DMC) and cyclohexane on the recovered yield of 2-hydroxy-4-methoxybenzophenone-5-sulphonic acid.

Experimental conditions were as described in Example 1.

| Example | DMC (%) | Cyclohexane (%) | Yield (%) |
|---------|---------|-----------------|-----------|
| 1 | 60 | 40 | 90 |
| 8 | 100 | 0 | 73 |
| 9 | 0 | 100 | Note 1 |
| 10 | 10 | 90 | Note 1 |
| 11 | 60 | 40 | 92 (Note 2) |
| 12 | 50 | 50 | 88 |
| 13 | 40 | 60 | 90 |

Note 1:
The product was coloured and very sticky - not isolatable.
Note 2:
Repeat of Example 1

What is claimed is:
1. A process for the preparation of sulphonated phenols of the general formula I

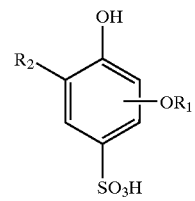

I where $R_1$ is hydrogen, a $C_1$–$C_{20}$ alkyl group which is unsubstituted or substituted by halogen, cyano, hydroxyl, $C_1$–$C_{20}$ alkoxy, $C_2$–$C_{20}$ alkoxycarbonyl, acyloxy and/or phenyl which is unsubstituted or substituted by $C_1$–$C_4$ alkyl, $C_1$–$C_4$ alkoxy and/or halogen, $R_2$ is hydrogen, $C_1$–$C_{20}$ alkyl or benzoyl of the general formula II

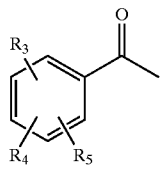

II where $R_3$ and $R_4$ independently of one another are each hydrogen, halogen, $C_1$–$C_{12}$ alkyl, $C_1$–$C_{12}$ alkoxy, $C_1$–$C_4$ haloalkyl, $C_3$–$C_8$ cycloalkyl, $C_4$–$C_{12}$ cycloalkylalkyl, cyano, hydroxyl, or hydroxyethyl or are each phenoxy, $C_7$–$C_{10}$ phenylalkyl or phenyl which is unsubstituted or substituted by $C_1$–$C_4$ alkyl, $C_1$–$C_4$ alkoxy and/or halogen, and $R_5$ is hydrogen or the group $SO_3X$ where X can be hydrogen, a monovalent metal or a group —$N(R_6)_3$, where each of the three radicals $R_6$ can be independently of one another hydrogen, $C_1$–$C_6$ alkyl or $C_1$–$C_6$ hydroxy alkyl which process comprises reacting a phenol of the general formula III

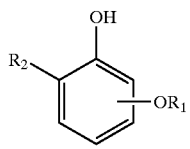

III where $R_1$ and $R_2$ are as defined above, with a halosulphonic acid in a solvent which is a mixture of a $C_5$–$C_{10}$ aliphatic or cycloaliphatic hydrocarbon and a dialkyl carbonate of the general formula IV

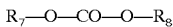

$R_7$—O—CO—O—$R_8$   IV where $R_7$ and $R_8$ each represent independently a $C_1$–$C_4$ alkyl group.

2. The process of claim 1 wherein the phenol of general formula III is catechol, resorcinol, hydroquinone or a benzophenone.

3. The process of claim 1 wherein the benzophenone is a 4-alkoxy-2-hydroxybenzophenone.

4. The process of claim 1 wherein the halosulphonic acid is chlorosulphonic acid.

5. The process of claim 1 wherein a dialkyl carbonate in the solvent mixture is selected from the group consisting of dimethyl carbonate, diethyl carbonate or diisopropyl carbonate.

6. The process of claim 1 wherein an aliphatic or cycloaliphatic hydrocarbon in the solvent mixture is selected from the group consisting of hexane, cyclohexane, methylcyclohexane, heptane, isooctane, isononane or decane.

7. The process of claim 1 carried out with an excess of the phenol of general formula III over the halosulphonic acid.

8. The process of claim 7 wherein there is provided in the reactants a 2 to 5 mol % excess of the phenol over the halosulphonic acid.

9. The process of claim 1 wherein the concentration of the phenol of general formula III in the solvent mixture is 5 to 50% w/w.

10. The process of claim 9 wherein the concentration of the phenol in the solvent mixture is 15 to 30% w/w.

11. The process of claim 1 wherein the dialkyl carbonate solvent and the aliphatic or cycloaliphatic hydrocarbon solvent are mixed in a weight ratio of from 10:90 to 90:10.

12. The process of claim 11 wherein the weight ratio of the dialkyl carbonate solvent to the aliphatic or cycloaliphatic hydrocarbon solvent is 40:60 to 60:40.

13. The process of claim 1 carried out at a temperature between −10° C. and 80° C.

14. The process of claim 13 wherein the sulphonation reaction is carried out at a temperature between 0° C. to 30° C. and the products of the sulphonation are then raised gradually to 60° C. to 70° C. to remove acid byproduct from the sulphonation reaction.

15. The process of claim 1 carried out at a pressure between 2 mm and 760 mm.

16. The process of claim 2 wherein the halosulphonic acid is chlorosulphonic acid.

17. The process of claim 16 wherein a dialkyl carbonate in the solvent mixture is selected from the group consisting of dimethyl carbonate, diethyl carbonate or diisopropyl carbonate.

18. The process of claim 17 wherein an aliphatic or cycloaliphatic hydrocarbon in the solvent mixture is selected from the group consisting of hexane, cyclohexane, methylcyclohexane, heptane, isooctane, isononane or decane.

19. The process of claim 18 wherein there is present in the reactants an excess of phenol of general formula III over the halosulphonic acid.

20. The process of claim 19 wherein the concentration of the phenol of the general formula III in the solvent mixture is 5 to 50% w/w.

\* \* \* \* \*